United States Patent [19]

Parab

[11] Patent Number: 5,374,633
[45] Date of Patent: Dec. 20, 1994

[54] IMIDAZOLE DERMAL PENETRATION ENHANCERS

[75] Inventor: Prakash Parab, Williamsville, N.Y.

[73] Assignee: Bristol-Myers Squibb Company, New York, N.Y.

[21] Appl. No.: 771,590

[22] Filed: Oct. 4, 1991

Related U.S. Application Data

[62] Division of Ser. No. 524,417, May 17, 1990, Pat. No. 5,087,620.

[51] Int. Cl.$^5$ .................. A61K 31/495; A61K 31/50
[52] U.S. Cl. ..................................... 514/252; 514/947
[58] Field of Search ............................... 514/252, 947

[56] References Cited

U.S. PATENT DOCUMENTS

| | | | |
|---|---|---|---|
| 4,298,604 | 11/1981 | Hammell et al. | 424/240 |
| 4,457,938 | 7/1984 | Von Bittera et al. | 514/396 |
| 4,621,095 | 11/1986 | Regel et al. | 514/383 |
| 4,632,932 | 12/1986 | Kramer et al. | 514/383 |
| 4,732,892 | 3/1988 | Sarpotdar et al. | 514/178 |
| 4,775,529 | 10/1988 | Sequeira et al. | 424/81 |
| 4,863,970 | 9/1985 | Patel et al. | 514/784 |
| 4,879,385 | 11/1989 | Elbe et al. | 514/383 |
| 4,912,124 | 3/1990 | Das et al. | 514/399 |

FOREIGN PATENT DOCUMENTS

| | | |
|---|---|---|
| 0270316A2 | 6/1988 | European Pat. Off. |
| 3243544 | 5/1984 | Germany . |
| 6064923 | 4/1985 | Japan . |

OTHER PUBLICATIONS

S. Bennett, et al., "Optimization of Bioavailability of Topical Steroids: Non-occluded Penetration Enhancers under Thermodynamic Control", *J. Pharm. Pharmacol.* 1985, 37:298–304.

*Primary Examiner*—Gary E. Hollinden
*Attorney, Agent, or Firm*—Anthony M. Santini; Sandra Nolan

[57] ABSTRACT

Topically administerable compositions are described which contain, in a pharmaceutically acceptable vehicle, a combination of a drug whose dermal penetration can be enhanced and a combination of substances, which combination enhances and controls the penetration of the compositions through the skin. The combination contains an antifungal amount of an imidazole and a certain amount of either propylene glycol, specified fatty acid ester(s) or a mixture of propylene glycol and specified fatty acid ester(s).

6 Claims, 3 Drawing Sheets

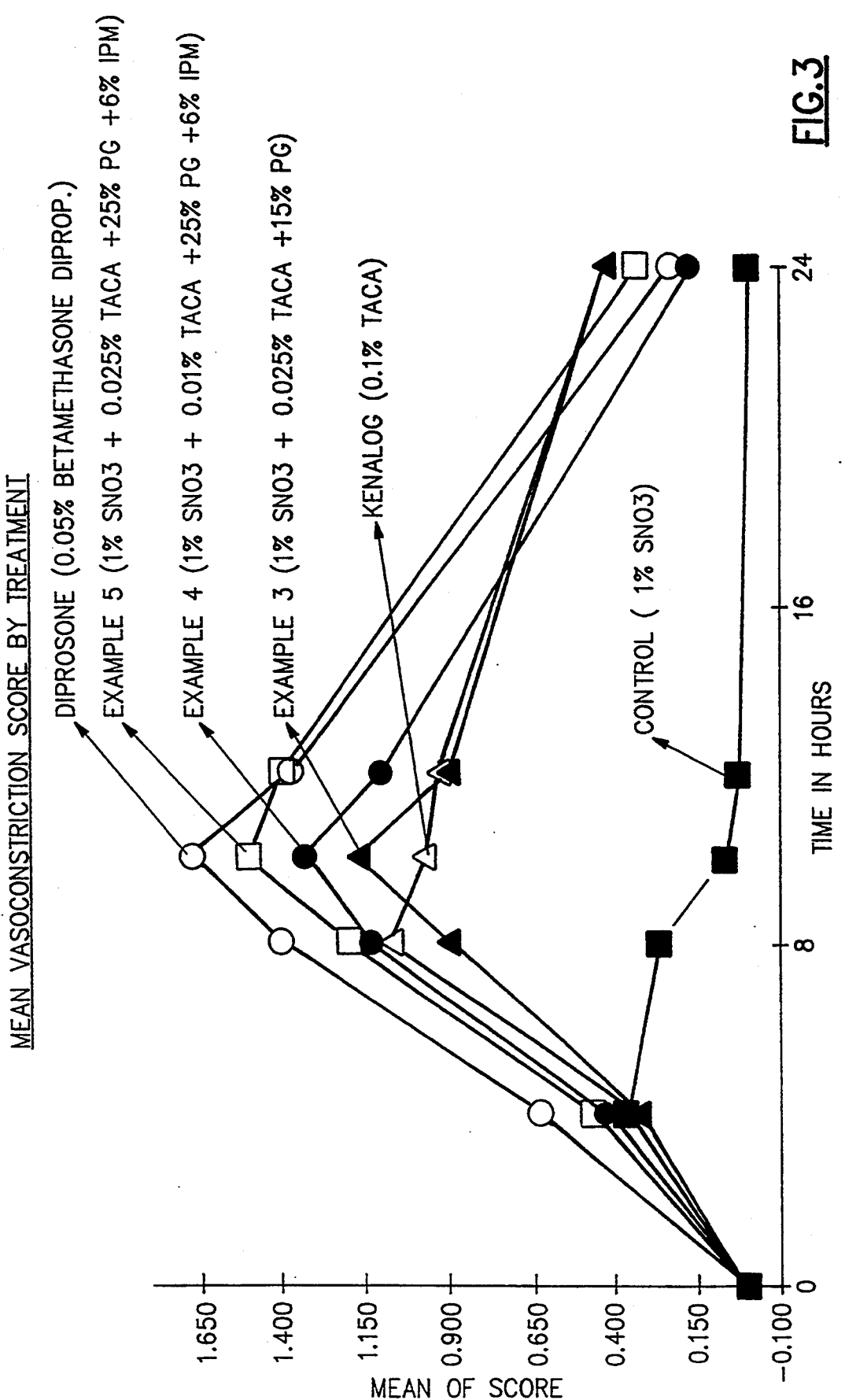

IMIDAZOLE DERMAL PENETRATION ENHANCERS

This application is a division of U.S. application Ser. No. 07/524,417 filed May 17, 1990 now U.S. Pat. No. 5,087,620.

RELATED APPLICATIONS

This application contains subject matter similar in some respects to that of copending and commonly owned patent application Ser. No. 353,890, filed May 22, 1989 which relates to enhanced transdermal penetration for systemic delivery of various topically applied pharmacologically active agents utilizing imidazole derivatives as penetration enhancing agents. It also contains subject matter similar, in some respects, to the subject matter of copending and commonly owned patent application Ser. No. 323,727, filed Mar. 15, 1989 which relates to topical compositions containing antiinflammatory 17-ester steroids together with imidazole compounds having antifungal activity.

FIELD OF THE INVENTION

This invention relates to controlled dermal penetration of various topically applied preparations. More specifically, the invention relates to compositions and methods for controlling the degree of dermal penetration of topically applied pharmacologically active agents utilizing compositions containing an antifungal amount of at least one antifungal imidazole together with a mixture containing at least one ester of a higher fatty acid such as isopropyl myristate (IPM) and defined quantities of propylene glycol (PG), or with PG alone provided that at least 15 wt % of this product is employed.

BACKGROUND OF THE INVENTION

Topical application of therapeutic agents has received and is presently receiving considerable attention. However, applicants are unaware of any teachings in the prior art of the use of combinations of an antifungal imidazole together with PG or a mixture of PG and IPM or equivalent ester to achieve controlled degrees of penetration of pharmacologically active agents through skin, particularly human skin.

U.S. Pat. No. 4,298,604 which issued on Nov. 3, 1981 describes topical compositions containing the corticosteroid betamethasone dipropionate and, as an antifungal agent, the imidazole derivative, clotrimazole.

European Patent Application 0 270 316 published Jun. 8, 1988 describes topical ache compositions containing 1-substituted imidazole antifungal agents such as tioconazole, clotrimazole, ketoconazole and econazole together with a non-steroidal antiinflammatory agent such as aspirin.

The above identified U.S. patent application Ser. No. 353,890 describes compositions and methods for transdermal penetration of a wide variety of therapeutic agents utilizing topical compositions containing imidazole and certain imidazole derivatives. According to the invention, there is complete penetration of skin with resulting systemic distribution of the therapeutic agent.

U.S. patent application Ser. No. 323,727 also cited above describes topical hydro-alcoholic formulations of 17-ester steroids stabilized in the presence of an antifungal agent such as an imidazole compound. The improvement in stability of 17-ester steroids is claimed to be due to the use of hydro-alcoholic compositions consisting of lower alkanol in combination with dihydroxy alcohol or a trihydroxy alcohol or a mixture thereof gelled with hydroxypropyl or hydroxyethyl cellulose. The application also attributes enhancement of skin penetration of imidazole and 17-ester steroid to lower alkanol such as ethyl alcohol.

SUMMARY OF THE INVENTION

The present invention is directed to lower ($C_1$–$C_4$) alkanol free topical compositions containing an effective amount of a pharmacologically active agent whose dermal penetration is capable of being enhanced for controlled dermal penetration of the selected agent. The dermal penetration controlling topical compositions contain an antifungally effective amount of an antifungal imidazole such as sulconazole nitrate ($SNO_3$), such amount being also sufficient to enhance dermal penetration of the pharmacologically active agent. The compositions additionally contain at least one reagent selected from the group consisting of at least 15 wt % PG, or IPM, and/or isopropyl isostearate and/or isopropyl palmitate together with PG.

The compositions of the invention contain selected quantities of the ester such as IPM together with PG, or PG alone provided that at least 15 wt % of PG is employed. PG is a good solvent for imidazoles and, when used together with IPM or equivalent ester, will inhibit precipitation of the imidazole.

The compositions of the inventions are useful for a wide variety of topical therapeutic treatments of mammals. They are especially useful for the treatment of various skin disorders such as candidiasis, tinea infections, dermatophytosis and adjunctly with other skin disorders such as psoriasis; ache and pigmentation which are thought to be associated with fungal infections.

The compositions are particularly characterized and are particularly beneficial in that, by selecting the respective amounts of the IPM and the PG it is possible to obtain a desired degree of penetration. Generally, the degree of penetration parallels the amounts of these reagents in the compositions. The higher the amounts, within the selected ranges, the higher the degree of penetration.

The compositions, when used with selected mid-potency steroids, obtain the advantageous activity of high potency steroids, without their undesirable attributes such as skin atrophy, rebound phenomenon and telangiectasia. It has been observed that with the compositions of the invention, potency generally increases with increased penetration. Thus mid-potency steroids may function as high potency steroids when formulated in compositions of the inventions which are designed for deep penetration.

Still another advantage is that the formulations can be modified to achieve desired degrees of penetration in thin skin areas such as the face and thick skin areas such as the palms of the hands and the soles of the feet.

The compositions may also contain other ingredients of the type commonly employed by those skilled in the art of compositions for topical application. These may include, for example, carriers, emollients, surfactants and the like. Such selected additives should preferably not substantially alter the dermal penetration properties of the topical compositions.

As used herein, the term "control of dermal penetration" refers to the ability to control the degree to which a pharmacologically active agent will penetrate the skin. It exludes complete penetration and systemic distribution of the agent. This ability to control penetration is an important addition to the armamentarium of the physician or veterinarian because of the ease of topical administration and the fact that certain therapeutic agents desirably act at various depths of the skin, e.g. the epidermis, the basal layer or the dermis. Additionally, the stratum corneum or outer layer of the epidermis thickens appreciably in certain types of psoriasis. It is important in the treatment of such types of psoriasis to maintain the active agent in proximity to the viable epidermis and dermis.

The term "pharmaceutically acceptable" generally means substantially non-toxic and, when applied to pharmaceutically acceptable acid addition salts, refers to non-toxic acid addition salts generally employed with alkaline therapeutic agents to improve their solubility, stability, or for some other purpose.

It includes organic acids such as citric, malic and lactic and inorganic acids, particularly mineral acids such as hydrochloric, sulfuric, nitric and phosphoric acids.

An "effective amount" of a specific pharmacologically active agent will vary in accordance with parameters well understood by the physician or veterinarian. These include, for example, the condition being treated, the age, weight and physical condition of the subject; and, of course, the specific agent selected. The compositions may contain two or more therapeutically active agents in addition to the antifungal imidazole including, for example a second antifungal agent such as griseofulvin.

It has been observed that an effective amount of triaminolone acetonide in the compositions of the invention is from about 0.001 wt % to about 0.5 wt %.

BRIEF DESCRIPTION OF THE DRAWINGS

FIGS. 1, 2 and 3 are graphs depicting the results of the experiments reported in certain of the examples.

DETAILED DESCRIPTION OF THE INVENTION

Figure 1:
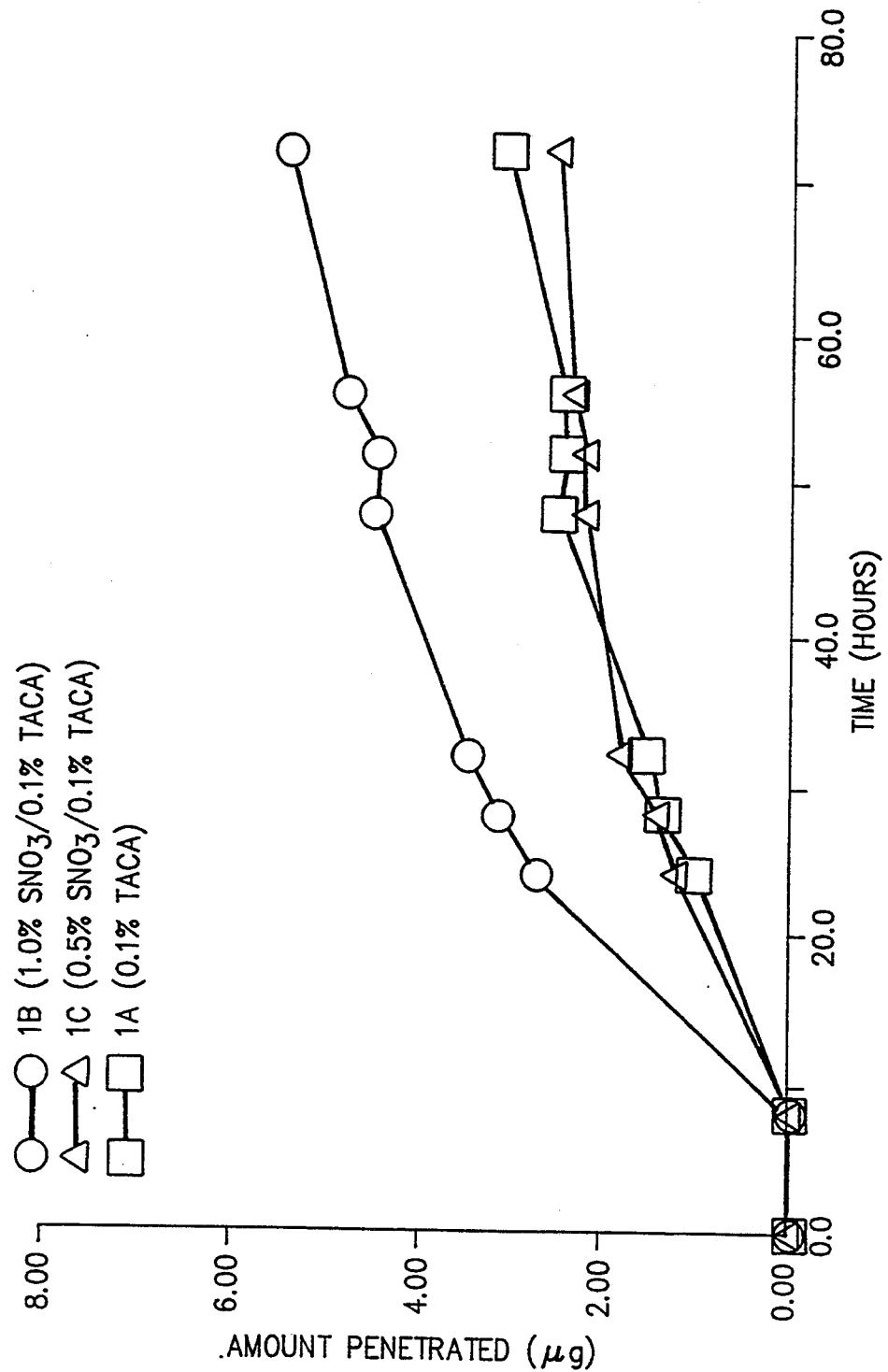

It has now been discovered that the dermal penetration of a pharmacologically active compound can be controlled by incorporating the compound into a mixture containing a dermal penetration controlling and antifungal amount of at least one antifungal imidazole together with PG and IPM, or at least 15 wt % of PG. It is unexpected to find these properties in lower alkanol free compositions.

The methods of this invention apply to topical compositions containing a wide variety of pharmacologically active agents including but not limited to:

Antihistamines such as tripelennamine, triprolidine, diphenhydramine and chlorpheniramine, antibiotics such as penicillins, cephalosporins, tetracyclines, polymixin B, bacitracin and novobiocin; antifungal agents such as nystatin, amphotericin B and griseofulvin; deodorants such as benzalkonium chloride; NSAIDS (non-steroidal antiinflammatory agents) such as aspirin, ibuprofen, phenylbutazone, and indomethacin; analgesics such as aspirin and ibuprofen; steroids such as hydrocortisone, prednisolone, betamethasone and triamcinolone; vasodilators such as hydralazine, enalopril maleate, minoxidil and nitroglycerin; dimenhydrinate and meclizine; and drugs for treating skin disorders such as anthralin, calcipotriol and retinoids.

The presently preferred antifungal imidazole compounds which may be employed in the practice of this invention are selected from the group consisting of:

| | |
|---|---|
| clotrimazole | imazalil |
| econazole | fenticonazole |
| miconazole | bifonazole |
| sulconazole | omoconazole |
| butoconazole | cloconazole |
| zinoconazole | sertaconazole |
| terconazole | peraconazole |
| oxiconozole | ketoconazole |
| bifonazole | SS-717 |
| tioconazole | TS-80 | pharmaceutically acceptable acid addition salts of said imidazole derivatives and mixtures of these compounds.

The more preferred compounds are clotrimazole, econozole, miconozole, sulconazole and non-toxic acid addition salts thereof. Of these, the most preferred, because it is easy to work with and readily available, is the nitric acid addition salt of sulconazole known as sulconazole nitrate ($SNO_3$).

While, as indicated above, the compositions and methods of this invention are useful with a very broad spectrum of pharmacologically active products, they are especially useful with compounds of the type often employed in topical creams, lotions, gels, ointments and the like. These include compositions containing antibiotics, antifungal agents, antiviral agents, retinoids, antipsoriasis agents and steroids, particularly antiinflammatory steroids such as hydrocortisone, prednisolone, 6 α-methyl prednisolone, fludrocortisone (9 α-fluorohydrocortisone), triamcinolone (9 α-fluoro-16 α-hyroxyprednisolone), paramethasone (6 α-fluoro-16 α-methylprednisolone), betamethasone (9 α-fluoro-16 β-methylprednisolone) 6 α-fluoro-clobetasol, clobetasol and dexamethasone (9 α-fluoro-16 α-methylprednisolone). The chemistry and physiological activity of these steroids is well known, as is the fact that they are often used in the form of the 17 - or 21 - esters of carboxylic acids or as acetonides. All such compounds are within the scope of this invention.

The topical activity of steroids is measured by the vasoconstriction assay. In the test, the ability of the steroids to cause blanching (an indication of vasoconstriction) is determined. The compounds under test are applied in the same carrier to the forearms of humans and the sites are covered with non-occlusive plastic guards for 20 hours. The sites are washed with water and the degree of blanching is evaluated at the test sites 3 to 4 hours later. Utilizing this test, steroids have been classified for topical activity as ultra high potency, high potency, mid-potency and low potency. The potency may depend upon the vehicle in which the steroid is applied and/or the concentration of the steroid in the vehicle, but as a general rule clobetasol is considered to be ultra high potency, betamethasone to be high potency, triamcinolone acetonide (TACA) to be mid-potency and hydrocortisone, prednisolone and methylprednisolone to be low potency.

This test can also be used as a measure of the degree of penetration of the steroid into the skin.

Another test often employed to determine the degree of dermal penetration is the skin stripping test. The isotopically labeled agent (radioactive) is applied to the skin of human or animal. Then, after a fixed period of time, the skin is stripped with successive adhesive tape application and removal. The tape strippings which have thin layer of skin removed are then analyzed to determine the depth of penetration.

All percentages of composition components recited are, unless otherwise indicated, weight percent (wt %) and are based upon the total weight of the composition.

As would be expected, some antifungal imidazoles utilized in this invention are more active than others for enhancing the degree of controlled penetration of the pharmacologically active agents in the composition of the invention. Thus, not all of them are useful at the same concentration level. Typically, however, the antifungal imidazoles are useful at concentration levels of from about 0.4 wt % to about 2 wt %. The presently preferred level for $SNO_3$ is from about 0.75 wt % to 1.5 wt %, with the optimum from about 0.9 wt % to 1.2 wt %.

The optimum level of PG and/or IPM for a particular antifungal imidazole derivative may be readily evaluated by a few simple tests such as those described herein.

At a fixed concentration of imidazole derivative in the compositions of the invention, the degree of penetration of the pharmacologically active agent may be controlled by the concentration of the PG and/or IPM. Generally the concentration of the IPM or equivalent ester is from about 2 wt % to about 30 wt %, preferably about 5 wt % to about 15 wt % and the concentration of PG is from about 0 wt % to about 60 wt % unless it is used alone. In that event the concentration is from 15 wt % to about 60 wt %. When utilized with IPM or equivalent ester the preferred concentration of PG is from about 10 wt % to about 35 wt %. To increase the depth of penetration, the concentration of PG and/or IPM will be increased. To decrease the depth of penetration, the concentrations will be decreased.

The following test method may be employed with human skin to determine topical penetration of pharmacologically active steroids used in the practice of this invention. The procedure is also applicable to pig skin and rat skin.

In Vitro Skin Penetration Study

Normal excised human skin samples obtained from breast reduction were used. Appropriate size specimens were frozen on the microtome with carbon dioxide and sectioned to a layer around 200 micrometers thick and stored in normal saline at 5° C. The skin sections were mounted on 9 mm inside diameter flat-top Franz diffusion cells. The diffusional cross-sectional area of the skin was 0.636 cm². A 50 microliter sample of a test formulation was placed on the skin in the donor compartment and the receiver compartment was filled with about 5 ml of normal saline (with pH adjusted to 4 with citric acid) and was well stirred. Water at 37.4° C. was circulated throughout the water jacket of the diffusion cell. A 100 microliter sample was withdrawn from the receiver compartment at appropriate intervals and analyzed for drug content by HPLC. The receptor fluid was replenished with normal saline after each withdrawal. All the receptor fluid and replenished fluid were thoroughly degassed before use.

The following examples are given by way of illustration only and should not be considered limitations of this invention.

EXAMPLES 1A–1C

The compositions shown below were prepared and tested utilizing the above described test procedure for human skin (in vitro). The results obtained are shown in FIG. 1 and recorded in Table 1.

|  | Example | | |
|---|---|---|---|
|  | 1A % w/w | 1B % w/w | 1C % w/w |
| Triamcinolone acetonide (TACA) | 0.1 | 0.1 | 0.1 |
| Sulconazole nitrate ($SNO_3$) | 0.0 | 1.0 | 0.5 |
| Propylene glycol (PG) | 25.0 | 25.0 | 25.0 |
| Isopropyl myristate (IPM) | 6.0 | 6.0 | 6.0 |
| Cetyl alcohol | 3.0 | 3.0 | 3.0 |
| Stearyl alcohol | 8.0 | 8.0 | 8.0 |
| Polysorbate 60 | 2.0 | 2.0 | 2.0 |
| Sorbitan monostearate | 1.0 | 1.0 | 1.0 |
| GMS SE (Glyceryl monostearate + Polyoxyethylene-100-stearate) | 3.0 | 3.0 | 3.0 |
| Ascorbyl palmitate | 0.02 | 0.02 | 0.02 |
| Sodium hydroxide | 0.0 | 0.08 | 0.04 |
| Citric acid | 0.007 | 0.00 | 0.00 |
| Purified water USP qs | 100.00 | 100.00 | 100.00 |

TABLE 1

$SNO_3$ AS A PENETRATION ENHANCER (HUMAN SKIN)

| EXAMPLE | $SNO_3$ and TACA COMPOSITION | 24 HOUR PENETRATION (TOTAL MICROGRAMS BASE*) | INCREASE IN PENETRATION RELATIVE TO CONTROL** |
|---|---|---|---|
| 1A | 0.1% TACA | 1.02 | — |
| 1B | 0.1% TACA + 1.0% $SNO_3$ | 2.70 | 2.6 |
| 1C | 0.1% TACA + 0.5% $SNO_3$ | 1.22 | 1.2 |

*Average of multiple determinations
**Multiple of average control determination

It will be observed that at all concentrations, after the passage of a sufficient period of time, there is penetration through the entire skin thickness of a varying degree, but only a small amount of the TACA. Penetration through the entire skin thickness is more rapid at the 1.0 wt % level of $SNO_3$. It will be apparent, also, that at all levels of $SNO_3$ there must be a concentration gradient such that the highest concentrations of active ingredient are towards the outer surface of the skin and the lowest concentrations are towards the inner surface. Therefore, a controlled penetration of the active components of the compositions has been achieved.

EXAMPLE 2

The vasoconstrictor activity of 1% $SNO_3$ and 0.1% TACA in a cream base as described in Example 1 and 1% $SNO_3$ and 0.05% TACA in the same cream base were compared in a double-blind within subject study with: (1) the cream base with 1% $SNO_3$ and no TACA (as a control) (2) TEMOVATE TM (0.05% clobetasol propionate) Cream (3) ELOCON TM (0.1% mometasone furoate) Cream, (4) MAXIVATE TM (0.05% betamethasone diproprionate) Cream, (5) KENALOG ™ (0.1% TACA) Cream, (6) ARISTOCORT ™ (0.1% TACA) Cream and (7) HYTONE ™ (1% hydrocortisone) Cream.

Equal amounts of each coded test medication (approximately 10 mg) were applied to 2 cm² sites on the volar forearms and left in place, unoccluded, for 8 hours. Vasoconstriction was assessed by grading the degree of blanching on a 4-point scale (none, mild, moderate, marked) at each test site at 4, 8, 10, 12 and 24 hours after application. Statistical analysis of the area under the curve (AUC) was conducted by ranking the AUC scores within each subject and performing an analysis of variance on the ranks (Friedman Test).

Thirty-five subjects (27 females and 8 males; all Caucasian) with an average age of 34.1 years were enrolled and completed the study. The mean ranks of the area under the curve (AUC) scores for each product reveal the following sequence of activity (from most to least); TEMOVATE, 1% $SNO_3$/0.1% TACA, 1% $SNO_3$/0.05% TACA, ELOCON Cream, MAXIVATE Cream, KENALOG Cream, ARISTOCORT Cream, HYTONE Cream and the cream base containing 1% $SNO_3$ and no TACA. The results indicate that the vasoconstrictor activity of the 1% $SNO_3$/0.1% TACA cream and the 1% $SNO_3$/0.05% TACA cream do not significantly differ. Both formulations are significantly more potent than MAXIVATE Cream, the high potency control, and significantly less potent that TEMOVATE Cream, the ultra-potency control. There were no adverse reactions.

Figure 2:
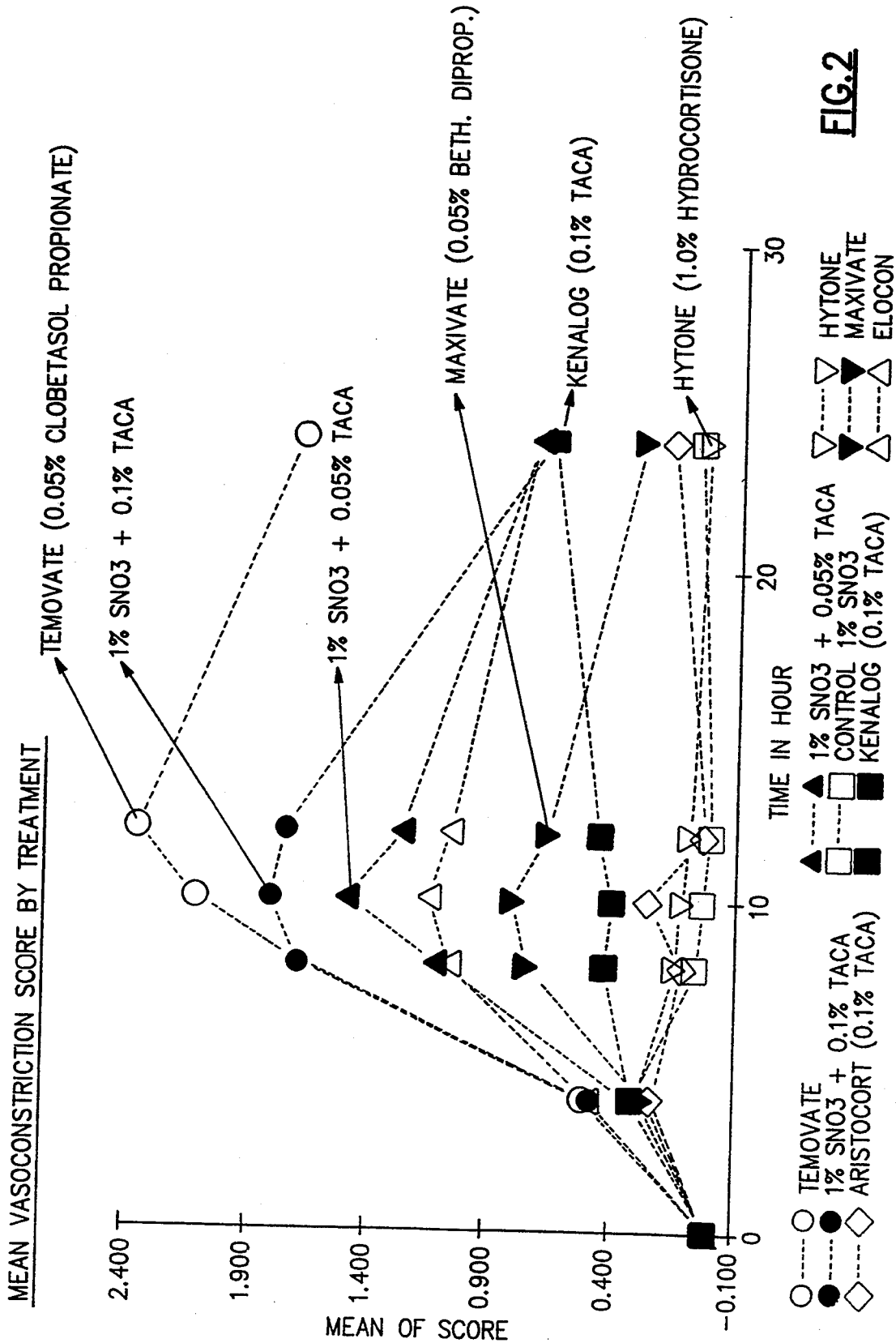

As stated heretofore, statistical analysis of the area under the curve (AUC) was conducted by ranking the AUC scores within each subject and performing an analysis of variance on the ranks (Friedman Test). Test products are listed in the following Table 2 with mean rank scores and mean AUC scores. FIG. 2 shows mean vasoconstriction score by treatment at different time intervals.

TABLE 2

| TEST PRODUCT | TUKEY'S STUDENTIZED RANGE TEST ON MEAN AUC RANK | MEAN AUC SCORE |
| --- | --- | --- |
| Temovate cream (ultra-potent steroid) | 9.54[A] | 37.86 |
| 1% Sulconazole nitrate + 0.1% TACA in cream base | 8.06[B] | 26.74 |
| 1% Sulconazole nitrate + 0.05% TACA in cream base | 6.91[BC] | 20.66 |
| Elocon cream | 6.46[C] | 19.09 |
| Maxivate cream | 4.66[D] | 11.17 |
| Kenalog Cream | 4.26[DE] | 10.49 |
| Aristocort cream | 3.00[EF] | 3.00 |
| Hytone cream | 2.71[F] | 2.57 |
| Cream base control containing 1% sulconazole nitrate and no TACA | 2.69[F] | 1.83 |

*Control - Base employed for 1% $SNO_3$ + 0.1% TACA and 1% $SNO_3$ + 0.05% TACA test products.
**Superscripts on numbers in columns with common letters do not significantly differ from each other as per Tukey's Test.

The Friedman Test for significant differences among treatments is significant at $P<0.0001$. The Tukey's Studentized Range Test is used to determine which treatments differ.

It is clear from the results obtained that inclusion of a dermal penetration controlling amount of $SNO_3$, PG and IPM with the TACA enables one to advantageously convert the medium potency steriod TACA to a high potency steroid.

EXAMPLES 3-5

This study was conducted to illustrate preferred formulations which utilize a dermal penetration enhancing amount of the imidazole derivative $SNO_3$ to increase the dermal penetration of the pharmacologically active steroid TACA. The formulations are designed to limit the extent of penetration to epidermis and dermis.

| | EXAMPLE | | |
| --- | --- | --- | --- |
| | 3 % W/W | 4 % W/W | 5 % W/W |
| PART A. | | | |
| Cetyl alcohol | 3.0 | 3.0 | 3.0 |
| Stearyl alcohol | 8.0 | 8.0 | 8.0 |
| Polysorbate 60 | 2.0 | 2.0 | 2.0 |
| Sorbitan monosterate | 1.0 | 1.0 | 1.0 |
| GMS SE (glyceryl monosterate + polyoxyethylene-100-stearate) | 0.3 | 0.3 | 0.3 |
| IPM | — | 6.0 | 6.0 |
| Mineral oil | 6.0 | — | — |
| PART B. | | | |
| PG | 12.0 | 20.0 | 20.0 |
| Sulconazole nitrate | 1.025 | 1.025 | 1.025 |
| Ascorbyl palmitate | 0.02 | 0.02 | 0.02 |
| PART C. | | | |
| PG | 3.0 | 5.0 | 5.0 |
| TACA | 0.03* | 0.013** | 0.03* |
| PART D. | | | |
| Disodium EDTA ($Na_2EDTA$) | 0.05 | 0.05 | 0.05 |
| Sodium hydroxide | 0.088 | 0.088 | 0.088 |
| Purified water USP qs | 100.00 | 100.00 | 100.00 |

*(containing 20% overage to allow for increased shelf life)
**(containing 30% overage to allow for increase shelf life)

1. The components of part A were mixed and the mixture was heated at 65°-70° C. until uniform.
2. Approximately 95% of the amount of water required was heated to 65° C.
3. The components of Part B were mixed and heated at 50° C. until uniform.
4. The components of Part C were mixed and heated to 50° C. until uniform.

The mixture of Step 1 was added to the water of Step 2 with rapid agitation to form an emulsion. When the emulsion temperature was about 50° C., the components of Step 3 were added.

6. The sodium hydroxide was dissolved in about 2.5 parts of the water, then added to the emulsion of Step 5 with continued mixing.

The pH of the emulsion of Step 6 was adjusted to 4.7–5.0 with the sodium hydroxide of Step 6.

7. When the temperature of the cream of Step 6 was about 40° C. the solution of Step 4 was added thereto.

8. The $Na_2$ EDTA was dispersed in the remaining 2.5 parts water then added to Step 7 with continued agitation until the temperature of the cream was decreased to 30° C.

It should be noted that the process outlined herein is preferred as it avoids heating $SNO_3$ and TACA together, which would cause decomposition of the TACA.

EXAMPLE 6

The compositions of Examples 3, 4 and 5 were tested in a vasoconstriction assay in comparison with DIPROSONE Cream (0.05% Betamethasone dipropionate), a high-potency control, and KENALOG Cream (0.1% Triamcinolone acetonide), a mid-potency control.

Results of the vasoconstriction assay (conducted in 30 healthy human subjects) are set forth in Table 3, below. FIG. 3 shows mean vasoconstriction by treatment at different time intervals.

The experimental design and statistics employed are as disclosed in Example 2.

TABLE 3

| TEST PRODUCT | TUKEY'S STUDENTIZED RANGE TEST ON MEAN AUC RANK | MEAN AUC SCORE |
|---|---|---|
| Diprosone cream (high potent steroid) | $7.20^A$ | 21.03 |
| 1% Sulconazole nitrate + 0.025% TACA in cream base with PG 25% and IPM 64 (Example 5) | $7.08^{AB}$ | 20.27 |
| 1% Sulconazole nitrate + 0.01% TACA in cream base with PG 25% and IPM 6% (Example 4) | $5.91^{ABC}$ | 16.50 |
| 1% Sulconazole nitrate + 0.025% TACA in cream base with PG 15% (Example 3) | $5.43^{BC}$ | 15.27 |
| Kenalog cream (mid-potent 0.1% TACA steroid) | $5.23^C$ | 15.60 |
| Cream base control containing 1% sulconazole nitrate and no TACA | $2.00^D$ | 2.63 |

*Superscripts on numbers in columns with common letters do not significantly differ from each other as per Tukey's Test The Friedman Test for significant differences among treatments is significant at $P<0.0001$. The Tukey's Studentized Range Test is useful to determine which treatments differ.

It is clear from the results shown in Table 3 that inclusion of a dermal penetration controlling amount of $SNO_3$, PG and IPM with TACA enables one to convert a mid-potent steroid to a high potency at a concentration three fold lower in comparison to the commercially available mid-potency product Kenalog cream containing 0.1% TACA.

It is also clear from Example 4 that such addition enables one to reduce the amount of TACA nine fold in comparison to Kenalog cream containing 0.1% TACA, while maintaining mid-potency activity.

By comparing Example 3 with Example 5 it is also clear that varying the amount of PG and IPM, enables one to control the rate and amount of penetration and hence vary the activity of 0.025% TACA from mid-potency to high-potency.

Thus by appropriate adjustment of the relative amounts of $SNO_3$ (or other dermal penetration controlling imidazole derivative in accordance with the present invention), isopropyl myristate and/or propylene glycol, one can tailor the formulation to obtain a desired degree of dermal penetration. When one couples this with appropriate adjustment of the level of TACA (or other pharmacologically active agent in accordance with the present invention), one can obtain a formulation having a desired potency and a desired degree of dermal penetration.

What is claimed is:

1. A lower alkanol free topical composition for controlled dermal penetration of a pharmacologically active agent contained therein comprising:
  (A) a pharmacologically effective amount of a pharmacologically active agent whose dermal penetration is capable of being enhanced,
  (B) an antifungal and dermal penetration controlling amount of an antifungal piperazine ring-containing imidazole which is a dermal penetration enhancer together with at least one reagent selected from the group consisting of from about 15 wt % to about 60 wt % of propylene glycol and from about 2 wt % to about 30 wt % of a fatty acid ester selected from the group consisting of isopropyl myristate, isopropyl isostearate and isopropyl palmitate together with from 0 wt % to 60 wt % of propylene glycol, and
  (C) a pharmaceutically acceptable topical vehicle.

2. The composition of claim 1 wherein the pharmacologically active agent is selected from the group consisting of antihistamines, antibiotics, antifungals, deodorants, NSAIDS, analgesics, antiinflammatory, steroids, retinoids, vasodilators, and agents for the treatment of abnormal skin conditions.

3. The composition of claim 1 wherein the imidazole dermal penetration enhancer is selected from the group consisting of terconazole and ketoconazole, pharmaceutically acceptable acid addition salts of said imidazoles and mixtures thereof.

4. A method of controlling the degree of dermal penetration of a pharmacologically active agent which comprises topical application of a lower alcohol free topical composition containing:
  (A) a pharmacologically effective amount of a pharmacologically active agent whose dermal penetration is capable of being enhanced,
  (B) an antifungal and dermal penetration controlling amount of an antifungal piperazine ring-containing imidazole which is a dermal penetration enhancer together with at least one reagent selected from the group consisting of from about 15 wt % to about 60 wt % of propylene glycol and from about 2 wt % to about 30 wt % of a fatty acid ester selected from the group consisting of isopropyl myristate, isopropyl isostearate and isopropyl palmitate together with from 0 wt % to 60 wt % of propylene glycol, and
  (C) a pharmaceutically acceptable topical vehicle.

5. The method of claim 4 wherein the dermal penetration enhancer is selected from the group consisting of clotrimazole, econozole, miconozole, sulconazole, butonazole, zinoconazole, terconazole, oxiconazole, bifonazole, tioconazole, imazalil, fenticonazole, omoconazole, cloconazole, sertaconazole, paraconazole, ketoconazole, SS-717 and TS-80, pharmaceutically acceptable acid addition salts of said imidazoles, and mixtures thereof.

6. The method of claim 4 wherein the pharmacologically active agent is selected from the group consisting of antihistamines, antibiotics, antifungals, deodorants, NSAIDS, analgesics, antiinflammatory, steroids, retinoids, vasodilators, and agents for the treatment of abnormal skin conditions.

* * * * *